(12) United States Patent
Nakanuma et al.

(10) Patent No.: US 6,715,915 B1
(45) Date of Patent: Apr. 6, 2004

(54) FLUIDITY DETERMINATION METHOD OF A PACKED FLUID AND DEVICE USED IN THE SAME

(75) Inventors: Hiroshi Nakanuma, Higashiyamato (JP); Nobuyuki Motoyoshi, Higashiyamato (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 0 days.

(21) Appl. No.: 09/807,566

(22) PCT Filed: Apr. 14, 2000

(86) PCT No.: PCT/JP00/02452

§ 371 (c)(1),
(2), (4) Date: Apr. 12, 2001

(87) PCT Pub. No.: WO01/13089

PCT Pub. Date: Feb. 22, 2001

(30) Foreign Application Priority Data

Aug. 13, 1999 (JP) ............................................. 11-229498

(51) Int. Cl.[7] ........................ G01N 25/00; G01N 11/00; G01K 3/08; G01K 3/06
(52) U.S. Cl. ......................... 374/54; 374/4.5; 374/110; 73/54.42; 73/54.01; 73/54.02
(58) Field of Search ............................. 374/120, 45, 54, 374/30, 150, 110, 112, 115, 153; 426/231–232; 73/54.01, 54.02, 54.42

(56) References Cited

U.S. PATENT DOCUMENTS

| | | | | |
|---|---|---|---|---|
| 4,583,868 A | * | 4/1986 | Girling | 374/114 |
| 4,603,979 A | * | 8/1986 | Matilainen et al. | 374/54 |
| 4,611,928 A | | 9/1986 | Hori et al. | 374/21 |
| 4,663,169 A | | 5/1987 | Hori et al. | 374/101 |
| 5,064,294 A | | 11/1991 | Cerf et al. | 374/16 |
| 5,341,672 A | * | 8/1994 | Kawanami et al. | 73/64.54 |
| 5,352,038 A | * | 10/1994 | Schmidt et al. | 374/45 |
| 5,615,953 A | * | 4/1997 | Moskal | 374/54 |
| 6,000,844 A | * | 12/1999 | Cramer et al. | 374/5 |
| 6,174,230 B1 | * | 1/2001 | Gerrity et al. | 453/57 |
| 6,261,244 B1 | * | 7/2001 | Kensey et al. | 600/573 |
| 6,286,992 B1 | * | 9/2001 | Kyrtsos | 374/45 |
| 2002/0007664 A1 | * | 1/2002 | Shin et al. | 73/54.07 |
| 2002/0169370 A1 | * | 11/2002 | Kensey et al. | 600/370 |

FOREIGN PATENT DOCUMENTS

| | | | |
|---|---|---|---|
| CA | 1 251 411 | 3/1989 | |
| CA | 2047426 | 3/1992 | .......... G01N/25/00 |
| DE | 3490255 C2 | 12/1984 | |
| DE | 1014694 A1 | * 3/2003 | .......... G01N/11/00 |
| DK | 034985 | 9/1925 | |
| DK | 75386 | 2/1953 | |
| EP | 0 144 443 | 6/1984 | |
| EP | 0 213 966 | 3/1987 | |
| FR | 2 626 371 | 8/1988 | |
| GB | 2259368 A | * 3/1993 | .......... G01N/11/00 |
| JP | 0046845 | * 3/1982 | ................. 374/112 |
| JP | 59-217162 | 12/1984 | |
| JP | 62-40246 | 2/1987 | |
| JP | 3-503449 | 8/1991 | |
| JP | 404016740 A | * 1/1992 | ................ 73/54.42 |
| JP | 6-229957 | 8/1994 | |
| WO | WO84/04813 | 12/1984 | |
| WO | WO89/06794 | 7/1989 | |

* cited by examiner

*Primary Examiner*—Gail Verbitsky
(74) *Attorney, Agent, or Firm*—Darby & Darby

(57) ABSTRACT

A method and device for determining fluidity of fluid in a pack that is moving without breaking and opening the pack by locating at least two measurement points on the surface of the pack filled with the fluid, measuring the surface temperatures of the measurement points by non-contact type temperature sensors, and managing the measured values using an arithmetic control unit.

15 Claims, 6 Drawing Sheets

FLUIDITY DETERMINATION METHOD OF A PACKED FLUID AND DEVICE USED IN THE SAME

TECHNICAL FIELD

The present invention relates to a fluidity determination method of a packed fluid and a device used in the fluidity determination method. More specifically, the present invention relates to a method for determining whether the fluidity of the packed fluid is high or low, whether the packed fluid is in a solid or liquid state, and whether the packed fluid is defective or non-effective, with high speed and without breaking or opening a pack, and a device used in this method.

BACKGROUND ART

In the food industry, fluids packed in various kinds of packs are sometimes used. When the packed fluids are manufactured, there is a case that the fluid having fluidity is filled with the pack, the fluidity of the fluid is changed, and the final product is completed.

For example, when desserts containing gelling agents such as a jelly are manufactured, a jelly raw material in a liquid state which is heated at high temperatures is packed, the fluidity thereof is gradually decreased by cooling using a refrigerator, and thereby the fluid is finally coagulated.

Moreover, "fluid" in the present specification means materials in a solid state having no fluidity, in addition to materials in a liquid state having fluidity. Therefore, a change of a fluid from a liquid state into a solid state or from a solid state into a liquid state is considered as a kind of fluidity change.

In the field of manufacturing packed fluid, the fluidity of the packed fluid is often strictly determined for production control.

For example, when the desserts containing gelling agents are shipped, if they are not sufficiently coagulated, and defective products are shipped, the trust of the consumers may be lost. Therefore, it is necessary to determine whether the products are defective or non-defective based on the fluidity level of the products.

As explained above, fluidity determination of the packed fluid has been important. In particular, in order to control production, a large scale factory is desired in which the products are continuously manufactured using transport lines such as a conveyor belt to determine the fluidity of some, preferably all, the packed products with high speed and without breaking or opening the pack. Moreover, it is also desired to always maintain the same level of accuracy in determining the fluidity when the environment changes due to a turn of seasons or when the environmental temperature changes due to a halt of machine operations in the factory.

For example, the following fluidity determination methods (I) to (IV) have been known in the food industry.

(I) a fluidity determination method in which a packed fluid is vibrated (Japanese Unexamined Patent Applications, First Publication Nos. Hei 02-236141 and Hei 10-033114);

(II) a fluidity determination method in which an agitation torque is measured when a liquid raw material of the fluid is agitated (Japanese Unexamined Patent Application, First Publication No. Hei 03-039061);

(III) a fluidity determination method in which the temperature, the electrical conductivity, etc. of a fluid are directly measured (Japanese Unexamined Patent Applications, First Publication Nos. Sho 59-217162 and Sho 62-040246, and Japanese Language Publication (Kohyo) Hei 03-503449 corresponding to PCT Patent Application); and (IV) a fluidity determination method in which the temperature of a fluid is measured without contact using a non-contact type temperature sensor (Japanese Unexamined Patent Application, First Publication No. Sho 61-032387).

However, a device for vibrating the pack is needed in the fluidity determination method (I); therefore, the entire device is complicated and large. There are problems with the fluidity determination method (I) in that the costs of investment and running increase, and furthermore system maintenance management is complicated. Moreover, time is required for the determination process; therefore, the fluidity determination method (I) is unsuitable for a continuous determination of the fluidity of the packed fluids on a continuous basis.

Agitation vanes are inserted into the fluid stored in a tank in the fluidity determination method (II); therefore, the fluidity determination method (II) cannot be used for packed fluids.

A sensor is directly inserted into the fluid or in thermal contact with the fluid in the fluidity determination method (III); therefore, it is difficult to carry out this method without breaking or opening the pack when the product is packed. Moreover, time is required for the determination process; therefore, the fluidity determination method (III) is unsuitable for production control in a large scale factory. Furthermore, heat, electricity, etc. are applied to the fluids; therefore, there is a possibility that the fluid will be denatured. The fluidity determination method (III) is unsuitable for determination of all products.

In the fluidity determination method (IV), a non-contact type temperature sensor is arranged in a heating device, an aluminum film covering an opening portion of the pack is covered with a synthetic resin film, and the heat conditions of the fluid are adjusted while the temperature of the synthetic resin film is measured without contacting the fluid. In the method (IV), the amount of heat applied to the fluid in the heating step is measured and adjusted. It is difficult to determine the fluidity of the fluid other than during the heating step; therefore, the fluidity determination method (IV) is unsuitable for production control in a large scale factory.

Moreover, in general, these fluidity determination methods (I) to (IV) are easily influenced by the temperature variation due to a turn of seasons and a halt of machine operations in the factory. Therefore, these fluidity determination methods (I) to (IV) cannot always determine the fluidity with a stable accuracy. In view of reliability, these methods are not suitable for production control in a factory.

As stated above, a simple fluidity determination method of packed fluids without breaking or opening the pack, in particular, which can be used on a continuous type large scale manufacture line, has not been established. Therefore, in the past, a method in which a sample of the packed fluid is periodically taken, opened, and the fluidity is determined has been chiefly used. The packed fluid used in this method must be discarded after determination.

DISCLOSURE OF INVENTION

It is an object of the present invention to provide a determination method for the fluidity of the packed fluid, which does not determine the fluidity of the sample packed fluids and which can determine the fluidity of all the packed fluid, without breaking and opening the pack and which have high speed. In addition, the determination method can determine the fluidity of the fluid with high accuracy, independent of the environment around the fluid. Furthermore, the structure of the use device is simple, and the costs of investment and running for the device are reduced.

The another object of the present invention is to provide a determination device for performing the determination method.

The first aspect of the present invention to be solved the problems is a determination method of the packed fluid comprising the steps of locating at least two measurement points on the surface of the pack, measuring the surface temperature of the pack at the located measurement points, and determining the fluidity of the fluid based on the measured surface temperature.

Moreover, the preferred embodiments of the first aspect of the present invention are the fluidity of the fluid is determined based on the difference between the surface temperatures of the pack at the two measurement points;

whether the fluidity of the fluid is in desired conditions is determined by comparing the difference between the surface temperatures with a predetermined standard value, and determining whether the fluidity of the fluid is in desired conditions based on whether the difference between the surface temperatures is larger than the standard value;

whether the fluidity of the fluid is in a solid or liquid state is determined by setting the standard value between the surface temperature difference of the fluid in a solid state and the surface temperature difference of the fluid in a liquid state, and determining whether the fluid is in a liquid or solid state based on whether the surface temperature difference is larger than the standard value;

the measurement points include a first measurement point located on the approximate center position of the side of the pack;

the measurement points include a second measurement point located above the first measurement point, other than the first measurement point;

the measurement of the surface temperature of the pack is performed under conditions in which there is a difference between the temperature of the packed fluid and the environmental temperature; and the measurement of the surface temperature of the pack is performed using a non-contact type temperature sensor.

The second aspect of the present invention to be solved the problems is a determination device for determining a fluidity of a packed fluid comprising at least (A-1) a non-contact type temperature sensor for measuring a surface temperature at a plurality of measurement points located at the different positions on the surface of the pack; and (A-2) an arithmetic means electrically connected with the non-contact type temperature sensor, which calculates a surface temperature difference at the two measurement points located at the different positions of the pack.

Moreover, the preferred embodiments of the second aspect of the present invention are the device further comprises (A-3) a defective product determination signal output means which compares the surface temperature difference calculated by the arithmetic means (A-2) with a predetermined standard value, and outputs the compared result as a defective product determination signal; and the device further comprises at least (A-4) a transport means for transporting the packed fluid after the measurement of the surface temperature of the pack by the non-contact type temperature sensor (A-1); and (A-5) a defective product discarding means for discarding the packed fluid transported by the transporting means (A-4) from a transporting line, in response to the defective product determination signal output from the defective product determination signal output means (A-3).

MODES FOR CARRYING OUT THE INVENTION

Figure 1:
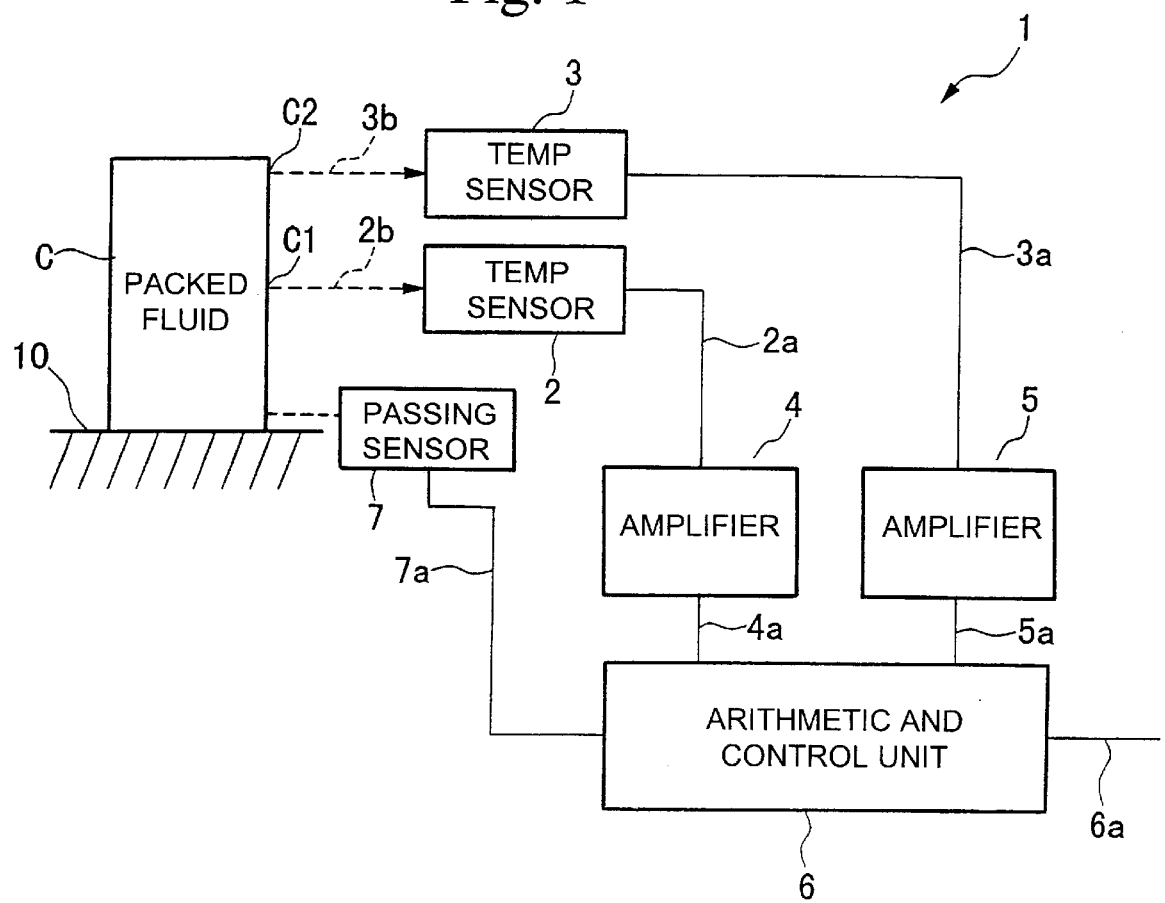
FIG. 1 is a block diagram showing a first embodiment of the device according to the present invention.

The method according to the present invention is characterized in that the temperature of at least two measurement points on the surface of a pack is measured and the fluidity of the fluid in the pack is determined based on the measured surface temperatures.

In the present method, the temperature of the fluid is not measured, but rather the surface temperature on the outside of the pack filled with the fluid is measured. When the fluidity of the fluid in the pack is high, the convection in the pack is active. Therefore, either the surface temperatures of some measurement points on the outside of the pack are substantially equal, or the surface temperature of the measurement point at the upward portion of the pack is higher than that of the measurement point at the lower portion, which is caused by a density difference in the fluid. In contrast, when the fluidity of the fluid is low, the difference between the surface temperatures at some measurement points on the outside of the pack increases, because convection of the fluid is nonactive, in proportion to a decrease in the fluidity. As described above, the fluidity of the fluid in the pack influences the temperature distribution on the surface of the pack. Therefore, it is possible to determine the fluidity of the fluid itself by examining the temperature distribution on the surface of the pack.

For example, a method, in which a contact type temperature sensor contacts the surface of the pack, can be adopted as a measurement method for the surface temperature of the pack. As the contact type temperature sensors, various kinds of sensors such as a thermistor type sensor, thermocouple type sensor, resistance thermometer, etc. can be exemplified.

In addition, a non-contact type temperature sensor can also be used. The non-contact type temperature sensors are not at risk of an abrasion, a degradation, etc. Moreover, the temperature can be measured while the packed fluid being transported at high speed. Therefore, the non-contact type temperature sensors are more preferable. As the non-contact type temperature sensors, various kinds of sensors such as a radiation thermometer, color thermometer, photoelectric thermometer, etc. can be exemplified. Radiation thermometers, in particular, infrared type radiation thermometers are most preferable.

As an example of a fluidity determination method based on the surface temperature of the pack filled with the fluid, there is a method in which the surface temperatures at a plurality of measurement points on the pack are measured and the temperature distribution on the surface of the pack is obtained by plotting the surface temperatures on a plane. According to this method, it is possible to determine whether the fluid is in desired conditions by judging whether the obtained temperature distribution shows that the fluid is in the desired conditions.

Moreover, the fluidity of the fluid can be determined by examining or calculating the difference between the surface temperatures at two measurement points. In other words, when the two measurement points are suitably located on the surface of the pack filled with the fluid as described below, a definite correlation between the difference between the surface temperatures at the two measurement points and the fluidity of the fluid in the pack can be obtained. Therefore, the fluidity of the fluid can be examined freely and analogously based on the difference between the surface temperatures at the two measurement points.

As described above, the surface temperature can be easily examined and calculated, the structure of the use device is simple, and the costs of investment and running for the device are reduced in the fluidity determination method of the fluid based on the difference between the surface temperatures at the two measurement points. Therefore, this fluidity determination method is more preferable.

Moreover, if the measurement point is suitably located, it is possible to partially determine a change in the fluidity of the fluid in the pack based on the temperature change at one measurement point on the surface of the pack; for example, whether the packed tofu is coagulated. However, when the surface temperature of the pack sometimes changes due to environmental temperature changes of the packed tofu, such as a turn of seasons, room temperature change, etc., the determination accuracy sometimes decreases in this case. Moreover, there is a possibility that the determination accuracy is delicately influenced by the temperature ununiformity of the fluid itself in the pack.

In contrast, when the fluidity is determined by locating the two measurement points and using the difference between the surface temperatures at these two measurement points, the influences due to the environmental temperature changes of the pack and the temperature ununiformity of the fluid are compensated. Thereby, the fluidity of the fluid can be always determined with the same level of accuracy.

In the present specification, "two measurement points" means a pair of measurement points used in obtaining the difference between the surface temperatures. Therefore, of course, there may be several pair of measurement points.

In order to determine the fluidity of the fluid using the two measurement points, the two measurement points are required to locate on the surface of the pack. It is preferable that one measurement point (the first measurement point) be located at the approximate center position of the side of the pack.

The present inventors found that when a fluid having a temperature higher than the environmental temperature is coagulated, the surface temperature at the center position of the side of the pack is the highest among the surface temperatures along the entire side of the pack, as disclosed in the following Test Examples.

Therefore, when the first measurement point is located at the approximate center position of the side of the pack, the surface temperature at the first measurement point is approximately the highest among the surface temperatures along the entire side of the pack. When other measurement points such as a second measurement point, etc. are located at the position at where the surface temperature is as low as possible, the difference between the surface temperatures at the first measurement point and the other measurement point is largest. When the measurement conditions are equal and the difference between the surface temperatures at the measurement points is larger, the fluidity of the fluid can be determined with a greater accuracy.

In contrast, when the temperature of the fluid is lower than the environmental temperature, for example, when cooled gels are placed in an ordinary temperature environment, and the fluid is coagulated, the surface temperature at the approximate center position of the side of the pack is the lowest. Therefore, it is possible to determine the fluidity with high accuracy by locating the first measurement point at the approximate center position of the side of the pack, similarly to that of the above-mentioned case.

Measurement point other than the first measurement point can be located on any suitable position. The position of the other measurement point can be selected based on the kind of fluid, the object of the fluidity determination, etc. However, the other measurement point is preferably located above the first measurement point.

As disclosed in the following Test Examples, when a fluid having a temperature higher than the environmental temperature is coagulated and in a solid state, the surface temperature at the first measurement point is the highest, and the surface temperature at the point above the first measurement point is lower than the surface temperature of the first measurement point. However, when the fluid is in a liquid state, the surface temperature above the first measurement point is higher than the surface temperature of the first measurement point. The surface temperature above the first measurement point varies, depending on whether the fluid is in a solid or a liquid state.

Therefore, when the second measurement point is located above the first measurement point, and the fluid is in a liquid state, the difference between the surface temperatures at these measurement points is extremely small. In contrast, when the second measurement point is located above the first measurement point, and the fluid is in a solid state, the difference between the surface temperatures at these measurement points is extremely large. Finally, when the second measurement point is located above the first measurement point, it is possible to determine with high accuracy whether the fluid is in a liquid or a solid state. Therefore, the second measurement point is preferably located above the first measurement point.

Moreover, for example, when the second measurement point is located on the side of the pack, the second measurement point is preferably separated from the first measurement point as much as possible. The second measurement point is most preferably located on the highest position on the side of the pack. Moreover, it is not necessary to locate these two measurement points on the same plane of the pack. For example, when the pack does not have a headspace, the second measurement point can be located on the top surface of the pack, rather than the side of the pack.

For example, when a raw material having a high temperature and a high fluidity is filled in the pack, cooled, and thereby it is coagulated, like a packed tofu coagulated in the pack as shown in the following Test Examples, it is preferable to locate the first measurement point at the approximate center position of the side of the pack and the second measurement point above the first measurement point. When the first and second measurement points are located on such positions and the tofu is defective which is not coagulated, the fluidity in the pack is high. Therefore, the difference between the surface temperatures of the first and second measurement points is small. In contrast, if the tofu is non-defective which is coagulated, the closer the point is to the center of the tofu, the higher the temperature is at that point. Therefore, the difference between the surface temperatures at the first and second measurement points is larger than the difference between the surface temperatures of the defective tofu.

Therefore, the coagulation condition of the packed tofu can be determined with high accuracy by examining the difference between the surface temperatures at the first and second measurement points.

Moreover, in order to suitably determine the fluidity, it is not always necessary to locate one measurement point at the approximate center position of the side of the pack.

For example, the coagulation conditions of tofu can be determined based on the difference between the surface temperatures at the second and third measurement points by locating the second measurement point at the vicinity of the highest position of the side of the pack and the third measurement point at the vicinity of the lowest position of the side of the pack. In this case, the surface temperature at the second measurement point varies, depending on whether the tofu is non-defective product which is coagulated or defective product which is not coagulated, as shown in the following Test Example (refer FIG. 3). However, there is not much difference between the surface temperature at the third measurement point when the tofu is non-effective and the surface temperature at the third measurement point when the tofu is defective.

Therefore, the coagulation conditions of the packed tofu can be determined with high accuracy by examining the difference between the surface temperatures at the second and third measurement points.

In order to determine the fluidity of the fluid using the difference between the surface temperatures at the two measurement points located as described above, it is preferable to determine whether the fluidity of the fluid is in desired conditions by comparing the difference of the surface temperatures with a pre-measured standard value, and judging whether the difference between the surface temperatures is larger than the standard value.

For example, when the determination of whether a packed fluid is non-defective or defective as a product is desired, the quality of the product can be determined by comparing the difference between the surface temperatures with a pre-measured standard value, and judging whether the difference between the surface temperatures is larger than the standard value. Specifically, when the fluidity of the packed fluid is larger and the fluid is a more preferable product, and the difference between the surface temperatures is larger than the standard value, the fluid is non-defective. When the difference between the surface temperatures is smaller than the standard value, the fluid is defective. In contrast, when the fluidity of the packed fluid is smaller and the fluid is a more preferable product, and the difference between the surface temperatures is larger than the standard value, the fluid is non-defective. Moreover, when the difference between the surface temperatures is smaller than the standard value, the fluid is defective. In other words, the fluidity of the packed fluid can be determined by comparing the difference between the surface temperatures with the standard value, depending on the determination style desired to the products.

Moreover, the standard value is not always only one; a plurality of standard values can be used. Furthermore, the fluidity can be determined by judging whether the difference of the surface temperatures is in a range from one standard value to another standard value.

In particular, when the packed fluidity changes from a liquid to solid state, or from a solid to liquid state in manufacturing processes, it is preferable to set the standard value to be between the difference between the surface temperatures when the fluid is in a solid state and the difference between the surface temperatures when the fluid is in a liquid state. In this case, whether the fluid is in a solid or liquid state can be easily determined by judging whether the difference between the surface temperatures is larger than the standard value.

For example, whether packed fat and oil in a solid state is coagulated, whether packed ice is dissolved, etc. are easily determined without breaking and opening the pack, according to the present invention.

Moreover, the present invention can be suitably used to determine whether liquid foods are completely coagulated in manufacturing processes in which liquid foods which contain a gelling agent and in a high temperature are filled in the pack, the pack is sealed, the pack is gradually cooled, and thereby the liquid foods are coagulated.

Furthermore, the fluidity determination method according to the present invention is preferably performed under conditions in which there is a difference between the temperature of the packed fluid and the environmental temperature. In the present specification, "the temperature of the packed fluid" means the temperature of the fluid itself which is in the pack. That is, the measurement of the surface temperature of the pack is preferably performed under conditions in which heat can be transferred to and from the fluid.

For example, when the packed fluid is refrigerated and then it is placed in a room temperature, heat is applied to the fluid through the pack, and the temperature of the packed fluid gradually rises. In this process, natural convection is noticeably generated in the fluid, the difference between the surface temperature distribution due to the difference of the fluidity increases, and thereby the accuracy of the fluidity determination increases.

In contrast, when a packed fluid at a high temperature is left in a room temperature and the packed fluid is cooled slowly, natural convection is also noticeably generated in the fluid, the difference between the surface temperature distribution due to the difference of the fluidity increases, and thereby the accuracy of the fluidity determination increases.

As an example of a method in which the difference between the temperature of the packed fluid and the environmental temperature is made large, there is a method in which a packed fluid is left alone and thereby the environmental temperature is made to change and a method in which the packed fluid is left alone at a room temperature after the packed fluid is placed in cooled water or hot water.

Specifically, the measurement of the surface temperature of the pack is preferably performed under conditions in which the difference between the temperature of the packed fluid and the environmental temperature is 5° C. or greater (9° F. or greater), and more preferably 10° C. or greater (18° F. or greater).

For example, measurement of the surface temperature of the pack is preferably performed by transporting the packed fluid from one environment to another environment in which the temperature difference between these environments is 9° F. or greater, and preferably 18° F. or greater, and by measuring the surface temperature of the pack before the packed fluid reaches to a thermal equilibrium. Immediately after transport, the difference in the temperature distribution due to the fluidity is small. Therefore, when the surface temperature of the pack is examined 10 minutes after the transport, the fluidity of the fluid can be determined with high accuracy. However, when the elapsed time after the transport is long, the fluid reaches a thermal equilibrium and the difference between the temperature of the packed fluid and the environmental temperature decreases. The measurement of the surface temperature a long time after the completion of the transport is not suitable. The suitable elapsed time after the transport depends on the size, thickness, and material of the pack. However, the fluidity determination is preferably performed within 60 minutes, more preferably 50 minutes, and most preferably 30 minutes after the transport.

As explained above, according to the fluidity determination method of the present invention, the fluidity of the packed fluid can be determined only by measuring the surface temperature of the pack. Therefore, the pack and the fluid are not subjected to physical procedures, such as a vibration, etc., as in conventional methods. As a result, high speed determination is possible, the structure of the use device can be simple, and the costs of investment and running for the device can be reduced.

Moreover, the fluidity of the packed fluid can be determined from the outside of the pack. Therefore, when the pack is sealed, the fluidity of the packed fluid can be determined without breaking and opening the pack. Furthermore, heat, electricity, etc. are not applied to the fluids; therefore, there is no possibility of the fluid being denatured. It is not necessary to periodically take and examine samples of the packed fluid. Therefore, the fluidity of all packed fluids can be determined. In addition, the determination process is fast, and the fluidity determination method of the present invention is suitable for control production when the packed fluids are continuously transported during manufacturing; it is therefore effective for quality control in the manufacturing site of a large scale factory.

Next, the determination device according to the present invention will be explained.

Figure 2:
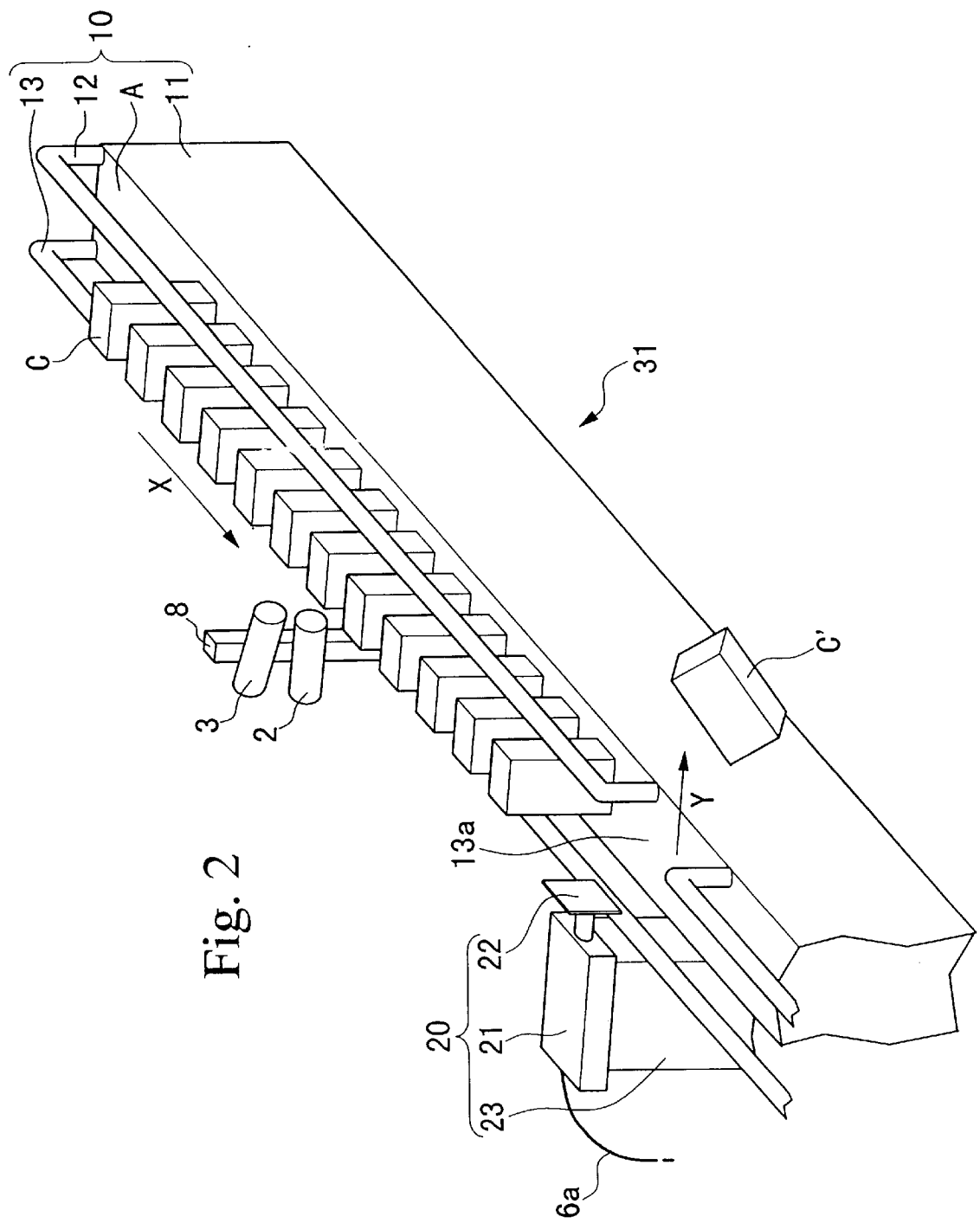
FIG. 2 is an outside drawing showing a second embodiment of the device according to the present invention.

FIG. 1 is a block diagram showing a first embodiment of the device according to the present invention. FIG. 2 is an outside drawing showing a second embodiment of the device according to the present invention. The determination device will be explained referring FIGS. 1 and 2. However, the technical scope of the present invention is not limited to the following embodiments.

The determination device 1 of the first embodiment comprises, as basic components, the non-contact type temperature sensors 2 and 3 for measuring the surface temperatures at the measurement points C1 and C2 which are located on different positions on the surface of the pack filled with the fluid C and the arithmetic and control unit 6 electrically connected to both non-contact type temperature sensors 2 and 3. Moreover, the determination device of this embodiment comprises the amplifiers 4 and 5 for amplifying the measured temperatures obtained by the non-contact type temperature sensors 2 and 3 and outputting them to the arithmetic and control unit 6. In FIG. 1, reference symbols 2a and 3a denote the sensor lines, and 4a and 5a denote the amplifier lines.

The packed fluid C is placed on the transport line such as a conveyor belt.

At least two measurement points are located on the surface of the pack filled with the fluid C. In this embodiment, the first measurement point C1 is located at the approximate center position of the side of the pack filled with the fluid C, and the second measurement point C2 is located above the first measurement point C1 as much as possible. Moreover, the second measurement point C2 is preferably located on the vicinity of the highest side of the pack. However, when the pack does not have a headspace, the second measurement point C2 can be located on the top surface of the pack.

The non-contact type temperature sensors 2 is located so as to be able to measure the surface temperature at the first measurement point C1, and the other non-contact type temperature sensor 3 is located so as to be able to measure the surface temperature at the second measurement point C2. In this embodiment, the infrared type radiation thermometer is preferably used as the non-contact type temperature sensors 2 and 3. In FIG. 1, reference symbols 2b and 3b denote the infrared radiation from the packed fluid C.

The arithmetic and control unit 6 comprises the arithmetic means for calculating the difference between the measured surface temperatures at the first and second measurement points C1 and C2.

Moreover, in this embodiment, the arithmetic and control unit 6 further comprises the defective product determination signal output means for comparing the difference between the surface temperatures calculated by the arithmetic means with the predetermined standard value and outputting the comparison result as a defective product determination signal. This defective product determination signal output means comprises a comparison circuit, comparator, comparison device, etc., which are well-known device.

The arithmetic means calculates the difference between the values measured by the non-contact type temperature sensors 2 and 3. In contrast, the defective product determination signal output means compares this difference with the standard value which is memorized, in advance. For example, when the difference between the measured values is larger than the pre-determined standard value, the defective product determination signal output means determines that the fluidity of the packed fluid C is lower than the desired fluidity, and outputs the defective product determination signal.

The defective product determination signal can be output via the output line 6a, for example. When a warning system, etc. is provided on the end of the output line 6a and a defective product is found, the detection of the defective products can be reported to a worker. Moreover, when the defective product determination signal is output to another control means (not shown in FIGS), etc., an automatic control depending on the fluidity can be performed.

As an example of the arithmetic and control unit 6, a personal computer, controller, signal processor, meter relay, analogue functional unit, etc. can be exemplified.

Moreover, the non-contact type temperature sensors 2 and 3 and the amplifiers 4 and 5 may be combined as a unit. In addition, the amplifiers 4 and 5 and the arithmetic and control unit 6 may be combined as a unit. Furthermore, the defective product determination signal output means and the arithmetic means can be separated.

The fluidity of the packed fluid C is determined using the determination device 1 of this embodiment as follows.

The surface temperature at the first measurement point C1 located on the side of the pack filled with the fluid C is measured by the non-contact type temperature sensor 2, and the measured result is input into the arithmetic and control unit 6 via the amplifier 4. Simultaneously, the surface temperature at the second measurement point C2 located on the side of the pack filled with the fluid C is measured by the other non-contact type temperature sensor 3, and the measured result is input into the arithmetic and control unit 6 via the amplifier 5. The arithmetic and control unit 6 calculates the difference between the surface temperatures at the first and second measurement points C1 and C2 based on these measured results. Then, the defective product determination signal output means compares the calculated difference between the surface temperatures with the prememorized standard value. When it determines that the fluidity is undesired, it outputs the defective product determination signal.

Moreover, in this embodiment, the non-contact type temperature sensors 2 and 3 measure the surface temperatures at the measurement points, and calculates the difference between the measured values. However, for example, it is possible that the surface temperature at one measurement point is judged as a standard temperature, and the comparative temperature with respect to the standard temperature is measured at the other measurement point. In other words, the functions of the non-contact type temperature sensors 2 and 3 and the functions of the arithmetic means can be combined as a unit, and thereby the difference between the surface temperatures can be detected in one step.

Furthermore, when the arithmetic and control unit 6 do not comprise the defective product determination signal output means, the suitable display means or recording means, such as a monitor, pen recorder, etc. can display the difference between the surface temperatures at the first and second measurement points C1 and C2, which is calculated by the arithmetic means, and the fluidity can be determined from the display.

Furthermore, a stationary examining table may be used instead of the transport means 10. Of course, the fluidity of the packed fluid C which is not transported can be determined.

When the packed fluid C is transported, a passing sensor 7 for sensing the passage of the packed fluid C through the temperature measurement position formed by the non-contact type temperature sensors 2 and 3 is preferably provided near the non-contact type temperature sensors 2 and 3. The signal from the passing sensor 7 is output to the arithmetic and control unit 6 via a cord 7a. The output signal timely instructs the arithmetic device to get the surface temperatures measured by the non-contact type temperature sensors 2 and 3.

As shown in FIG. 2, in order to automatically discard defective products, a determination device 31 of a second embodiment according to the present invention further comprises a defective product discarding means 20, in addition to the determination device 1 shown in FIG. 1.

That is, the determination device 31 of this embodiment comprises the transport means 10 having the appearance shown in FIG. 2 and the defective product discarding means 20 for discarding the defective products from the transport line A, in response to the defective product determination signal, in addition to the non-contact type temperature sensors 2 and 3, the amplifiers 4 and 5, the arithmetic and control unit 6, the sensor lines 2a and 3a, the amplifier lines 4a and 5a, the passing sensor 7, and the cord 7a, which are similar to those of the determination device 1 shown in FIG. 1. Moreover, some of the components comprising the determination device 31, which are the same as the components comprising the determination device 1 shown in FIG. 1, have been omitted in FIG. 2.

As the transport means 10, a conveyor belt, conveyor roller, conveyor chain, slider, etc. can be exemplified. In this embodiment, the conveyor belt 10 is preferably used. The belt surface of crawler conveyor belt 10, which is the transport line A, moves in the direction indicated by the arrow X in FIG. 2. The packed fluids C are placed on the transport line A (the belt surface) of the conveyor belt 10, and they are continuously transported in the direction indicated by the arrow X. Moreover, guards 12 and 13 for preventing the packed fluid C from falling off the transport line A are provided on both sides of the transport line A.

Moreover, the conveyor belts 10 similar to the conveyor belt 10 shown in FIG. 2, are provided at the upstream and downstream of the conveyor belt 10. However, the conveyor belts 10 provided at the upstream and downstream are omitted.

The defective product discarding means 20 discards the defective product C' from the transport line A. The structure of the defective product discarding means 20 can be suitably selected, depending on the form of the packed fluid C and the structure of the transport means 10. As the defective product discarding means 20, a device which discards the defective product C' by ejecting compressed air and blowing the defective product C', a device which moves the defective product C' from the transport line A to other transport line by operating the guard provided on the transport means 10, a pusher which pushes the defective product C' from the transport line A by reciprocating motion, etc. can be exemplified. Moreover, other well known devices can be also used as the defective product discarding means 20.

In this embodiment, the defective product discarding means 20 comprising the pusher 22 for pushing the defective product C' off of the transport line A by reciprocating motion, which is arranged on a main body 23 and a cylinder 21 for reciprocating the pusher 22 is used. Moreover, a gap 13a is provided with the guard 13 so that the pusher 22 of the defective product discarding means 20 can move advance (in the direction indicated by the arrow Y). The defective product C' is pushed off of the transport line A through the gap 13a. The defective product discarding means 20 is electrically connected the arithmetic and control unit 6 (not shown in FIG. 2; and refer to FIG. 1) via the output line 6a.

The non-contact type temperature sensors 2 and 3 are provided and secured to the stand 8.

The determination of the fluidity of the packed fluid C and the automatic discarding of the defective products, which use the determination device 31, are performed as explained below.

The packed fluid C is transported in the direction indicated by the arrow X by the conveyor belt 10. When the packed fluid C passes the non-contact type temperature sensors 2 and 3, the passing sensor 7 (refer FIG. 1) senses the packed fluid C, and outputs the signal to the arithmetic and control unit 6. The arithmetic and control unit 6 receives the signal, and the arithmetic means gets the measured surface temperatures at the two measurement points (C1 and C2 shown in FIG. 1) located on the packed tofu C. Then the arithmetic means processes the data, in accordance with the preprogrammed steps. As a result, whether the packed fluid C is non-defective or defective is determined. When the packed fluid C is determined to be a defective product, the defective product determination signal is output to the output line 6a.

The defective product determination signal is input into the defective product discarding means 20 via the output line 6a. The defective product discarding means 20 operates the cylinder 21, in response to the input defective products discarding signal. Thereby, the pusher 22 advances in the direction indicated by the arrow Y, and pushes the defective product C' off of the transport line A through the gap 13a. After that, the pusher 22 immediately goes back, and returns to its original position.

Moreover, a position sensor (not shown in FIGS) for sensing the passage of the defective product C1 is preferably provided with the defective product discarding means 20. As the position sensor, a photoelectric tube, etc, can be exemplified. The position sensor is preferably located at the position where the defective product discarding means 20 is located or where is the upstream with respect to the defective product discarding means 20. When the position sensor is located at the upstream with respect to the defective product discarding means 20, the time interval between when the position sensor senses the packed fluid C and when the packed fluid C reaches the defective product discarding means 20 is memorized as a time lag, in advance. When the position sensor senses the defective packed fluid C', the defective product discarding means 20 acts after the time lag has elapsed.

Moreover, the control device (not shown in FIGS) for operating the defective product discarding means 20 can be combined with the arithmetic and control unit 6 as a unit.

As explained above, according to the determination device 31 of this embodiment, the packed fluid C is transported by the transport means 10, the surface temperatures of the pack are measured by the non-contact type temperature sensors 2 and 3, and the defective product determination signal output means directly determines whether the packed fluid is defective. During these processes, after the measurement of the surface temperature, the packed fluid C is further transported by the transport means 10, and reaches the defective product discarding means 20. When the packed fluid C is determined to be a defective product, the packed fluid is automatically discarded by the defective product discarding means 20 from the transport line A.

Therefore, it is possible to respectively and directly determine whether the packed fluid C which is quickly and continuously transported is defective, and automatically discard only the defective product C' from the transporting line A.

The fluids determined by the present invention are not specifically limited. The present invention can widely determine the fluidity of a wide range of products, such as a product in a solid or liquid state. However, the present invention is preferably applied to the packed products, in particular, the packed foods. As the packed product, various kinds of foods which are considered that the coagulated state is non-defective, such as a jelly, tofu, yogurt, pudding, etc. and which are considered that the coagulated state is defective, such as milk, juice, etc. can be exemplified.

EXAMPLES

Below, the details of the present invention will be explained referring Examples; however, the present invention is not limited to the following Examples.

Example 1

The determination device 1 shown in FIG. 1 was formed. The determination device 1 determines the coagulation state of the packed tofu as the packed fluid C.

The conveyor belt was used as the transport means 10, and the packed tofu C was placed on the conveyor belt.

Two measurement points C1 and C2 were located on the side of the pack filled with tofu C. The one measurement point C1 was located at the approximate center position of the side of the pack. The other measurement point C2 was located on the highest position of the side of the pack.

The infrared type radiation temperature sensors (manufactured by Tokyo Seikou Co.; trade name: NT-LS215A) were used as the non-contact type temperature sensors 2 and 3. The temperature sensors 2 and 3 were arranged far from the side of the packed tofu at a distance of 100 mm. The temperature sensor 2 faced toward the measurement point C1 so as to detect the infrared radiation 2b. The other temperature sensor 3 faced toward the measurement point C2 so as to detect the infrared radiation 3b. The optical axis (measurement area) of the infrared radiation was 8 mm in diameter.

A signal processor (manufactured by Omron; trade name: K3TS) was used as the arithmetic and control unit 6. The signal processor 6 calculates the difference between the surface temperatures at the measurement points C1 and C2 of the packed tofu C, compares the calculated difference of the surface temperatures with the pre-determined standard value, and outputs the compared result to the output line 6a.

A fiber sensor 7 (manufactured by Keyence; trade name: FU-77, FS-V11) was used as the passing sensor 7. The fiber sensor 7 senses the passage of the packed tofu C through the irradiation position of the temperature sensors 2 and 3, and sends a trigger output.

In the determination device 1 of this Example, the temperature sensors 2 and 3 measure the surface temperatures at the measurement points C1 and C2 located on the packed tofu C. The measured results are input into the amplifiers 4 and 5, via the sensor lines 2a and 3a. The measured results are amplified in the amplifiers 4 and 5, and then output to the signal processor 6 via the amplifier lines 4a and 5a.

When the trigger informing the passage of the packed tofu C is input into the signal processor 6 from the fiber sensor 7, the signal processor 6 gets the measured values by the temperature sensors 2 and 3, starts to operate, calculates the difference between the surface temperatures, and compares the difference with the pre-memorized standard value, in response to the trigger. Moreover, the standard value was set to be between the surface temperature difference of the packed tofu in a solid state and that of the packed tofu in a liquid state.

When the difference between the measured surface temperatures is larger than the standard value, the signal processor 6 judges that the tofu C in the pack is sufficiently coagulated, and does not start to operate. In contrast, when the difference is smaller than the standard value, the convection is generated in the tofu C in the pack. Therefore, the signal processor 6 judges that the tofu in the pack is not sufficiently coagulated, and outputs a defective product determination signal to the output line 6a.

As explained above, the determination device 1 of this Example determines whether the packed tofu C is defective or non-defective by placing the packed tofu C on the conveyor belt 10, transporting, and detecting the infrared radiation 2b and 3b from the packed tofu C. When the packed tofu is defective, the determination device 1 outputs a defective product determination signal.

Therefore, the packed tofu C is not denatured. In addition, whether the packed tofu C is defective or non-defective can be determined with a remarkably high speed and without breaking or opening the pack.

Below, an example of the determination method of the present invention will be explained.

Preparation Example 1 for the Packed Tofu 6000 kg (solid content: 11.0%) of soybean milk prepared in an ordinary manner was sterilized by keeping the soybean milk at 298° F. for 3 seconds using a direct steam heat type sterilizer (manufactured by APV Co.; trade name: Uperization sterilizer), homogenized by cooling to 176° F., further cooled to 59° F., and stored in the axenic tank.

The stored soybean milk was aseptically flown in the pipe. 0.4% by weight of the coagulating agent solution, which is aseptic treated by the millipore membrane filter, was uniformly added to 100% by weight of the soybean milk. Then, the mixture was aseptically stored in a 300 ml of pack using an aseptic filling machine (manufactured by Tetrapack Co.; trade name: Aseptic Brick Filling Machine), sealed, and thereby the packed tofu was produced.

The obtained packed tofu were continuously transported by the conveyor belt, continuously placed in a warm water pool at 176° F., and thereby the tofu were coagulated. After that, the packed tofu were placed in the cold water pool, cooled to 86° F., and the surfaces of the packs were dried by continuously blowing air.

Test Example 1

In order to examine where the measurement point should be located on the surface of the pack to determine the fluidity with the highest accuracy, the following tests were performed.
1) Test Samples The packed tofu obtained in the Preparation Example 1 was used as a test sample. Moreover, two kinds of samples comprising a non-defective product which was sufficiently coagulated tofu and the defective product which was not sufficiently coagulated tofu were prepared.
2) Test Method After the packed tofu was heated and coagulated, it was left alone at a room temperature while the temperature of the tofu is maintained at high temperatures. The temperature distribution on the side of the pack was visualized using the thermography (manufactured by JEOL Co.; trade name: JTG6300).

Figure 3A:
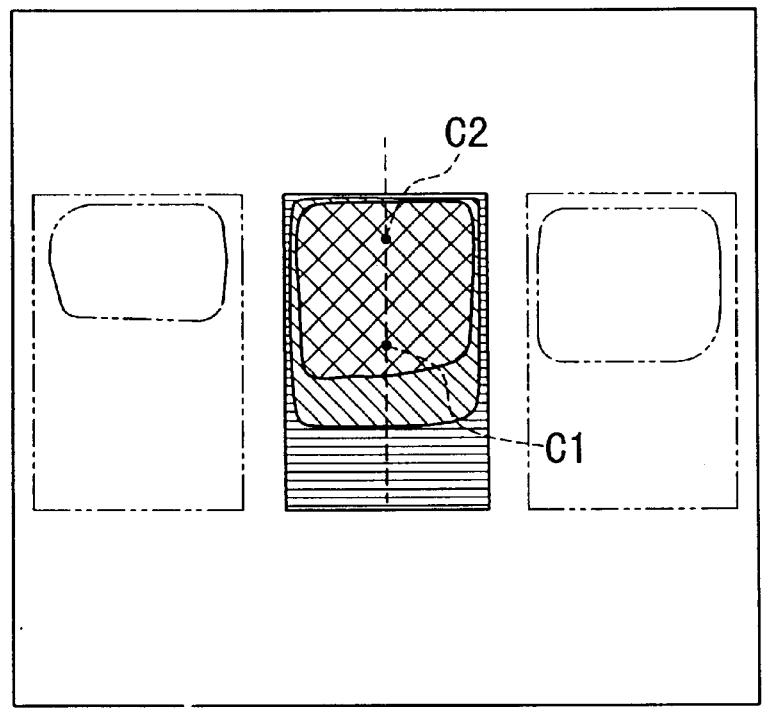
FIG. 3 is a thermogram showing a visualized temperature distribution on the surface of the pack filled with tofu.
Figure 3B:
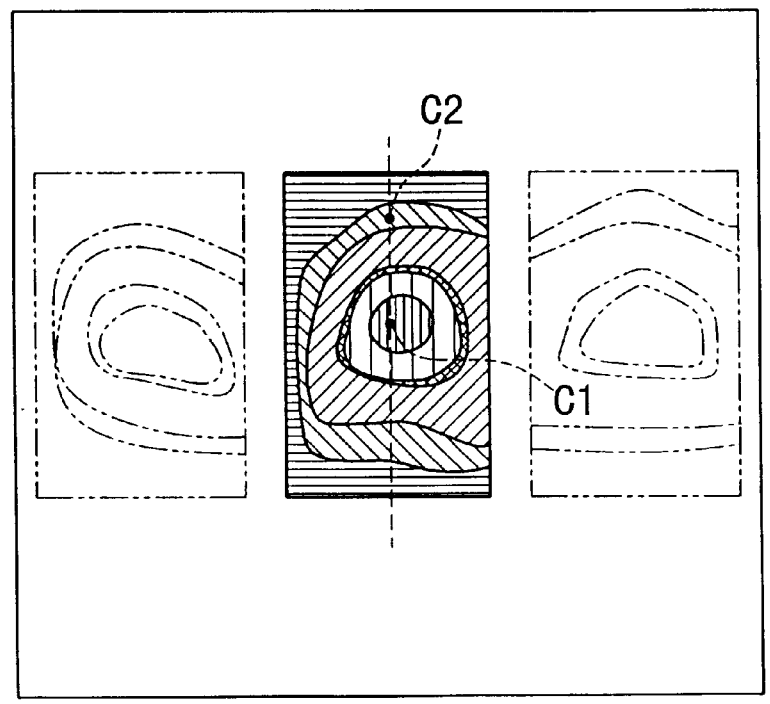

Such visualizing operations were performed using the non-defective products which were sufficiently coagulated tofu and the defective products which are not sufficiently coagulated tofu, and the obtained results were compared. Specifically, the measurement point C1 was located at the approximate center position of the side of the pack, and the measurement point C2 was located in the vicinity of the highest position of the pack and is on a line perpendicular to the measurement point C1. The temperature distribution at the measurement points C1 and C2 were compared.
3) Test Results The test results are shown in FIG. 3. FIG. 3 is a thermogram showing a visualized temperature distribution on the surface of the pack filled with tofu. FIG. 3(A) is a thermogram of the defective packed tofu which is not sufficiently coagulated, and FIG. 3(B) is a thermogram of the non-defective packed tofu which is sufficiently coagulated. In FIG. 3, the temperatures of the areas referenced with the identical symbol are substantially equal.

It is clear from FIG. 3(A) that when the coagulation of the packed tofu is imperfect, the tofu is in a liquid state and the convection is generated in the pack. Therefore, the temperatures in the area around the measurement point C1 at the center of the side of the pack and the area above the measurement point C1 are substantially equal. In other words, it is clear that the temperatures at the measurement points C1 and C2 are substantially equal, and there is not a difference between the temperatures at the measurement points C1 and C2 in FIG. 3(A).

In contrast, the packed tofu is completely coagulated; therefore, the area having the same temperature spreads so as to form a concentric circle the center of which is the measurement point C1 in FIG. 3(B). The temperature at the center of the concentric circle is the highest.

In other words, FIG. 3(B) shows that the measurement point C1 is at the center of the concentric circle; therefore, the surface temperature at the measurement point C1 is the highest. The measurement point C2 is positioned at the periphery of the concentric circle; therefore, the surface temperature at the measurement point C2 is lower than that at the measurement point C1. The difference between the surface temperatures at the measurement points C1 and C2 is remarkably large.

As a result of this test, it was confirmed that when the first measurement point C1 was located at the approximate center position of the side of the pack and the second measurement point C2 was located above the measurement point C1, the fluidity of the packed fluid, in particular, whether the fluid was in a liquid or solid state could be determined with high accuracy.

Moreover, tests using other fluids were similarly performed under different temperature conditions, and similar results were obtained.

Test Example 2

In order to examine the influence of the magnitude of the difference between the surface temperatures at the measurement points C1 and C2 on the accuracy of the fluidity determination, the following tests were performed.
1) Preparation of Samples The packed tofu obtained in the Preparation Example 1 was used as a test sample. Moreover, two kinds of samples comprising the non-defective product which was sufficiently coagulated tofu and the defective product which was not sufficiently coagulated tofu were prepared.
2) Test Method The surface temperature of the packed tofu was measured using the determination device 1 of the Example 1. Moreover, the determination of whether the packed tofu is non-defective or defective based on the measurement results was not performed. The difference between the surface temperatures calculated by the arithmetic means was output to the recorder, and recorded.

The immediate packed tofu after heat coagulation and cooling were continuously transported by the conveyor belt 10 and the surface temperature of the pack was measured. The positions of the measurement points C1 and C2 were the same as those of the measurement points C1 and C2 in the Test Example 1 above.

The transport speed of the conveyor belt was set to 23 m/min. The signal processor 6 sampled the difference between the measurement values of the temperature sensors 2 and 3 at a frequency of 1 kHz. After the input of the trigger from the passing sensor 7, the signal processor 6 calculated the average of 8 times of samplings. The average of 8 times of samplings was set as the standard value. Moreover, the transport distance of the packed tofu for 8 times of samplings was 3 mm.

As explained above, the difference between the surface temperatures at the measurement points C1 and C2 of 245 packed tofu was examined.

3) Test Results

Figure 4:
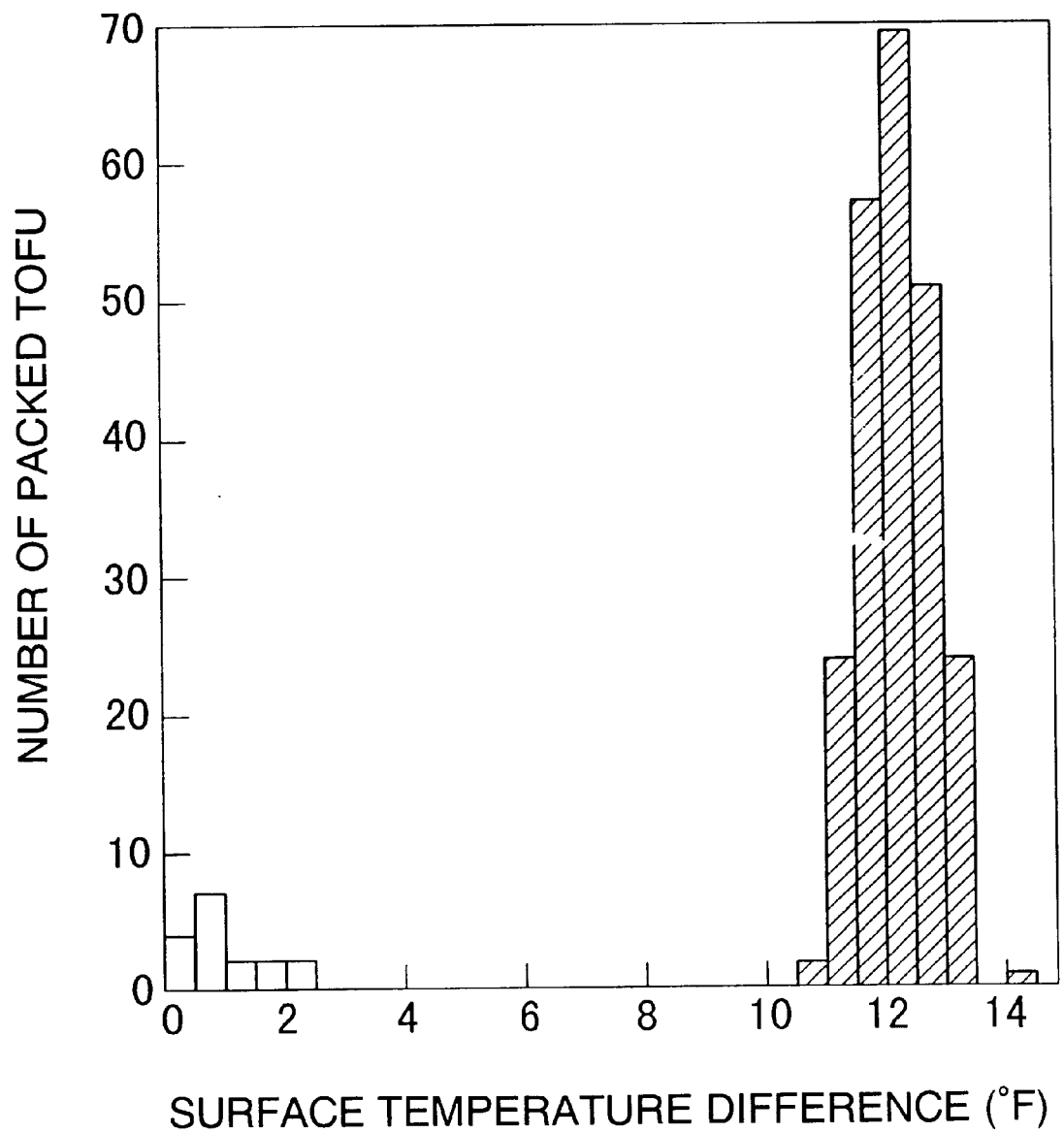
FIG. 4 is a graph showing a relationship between the difference between surface temperatures of packed tofu and a number distribution.

The test results are shown in FIG. 4. FIG. 4 is a graph showing the relationship between the difference of the surface temperatures of packed tofu and the number distribution of the packed tofu.

In FIG. 4, the transverse axis shows the difference between the surface temperatures at the measurement points C1 and C2, and the longitudinal axis shows the number of packed tofu having the difference between the surface temperatures shown in the transverse axis. In FIG. 4, the bar marked with diagonal lines denotes the non-defective product which was completely coagulated, and the bar with no marks denotes the defective product which was not completely coagulated.

It is clear from FIG. 4 that the difference between the surface temperatures at the measurement points C1 and C2 of all non-defective product which is completely coagulated (the bar marked with diagonal lines) is in a range from 10° F. to 15° F. In contrast, the difference between the surface temperatures at the measurement points C1 and C2 of all defective product which is completely coagulated (the bar with no marks) is less than 3° F.

It is clear from such results that whether the coagulation of the packed tofu is sufficient can be determined with high accuracy by setting the standard value in a range from 3 to 10° F., and by judging that the product is non-defective when the difference between the surface temperatures is larger than the standard value, and the product is defective when the difference is smaller than the standard value. As this test result, it was proved that the fluidity of the fluid could be determined with high accuracy according to the present invention.

Moreover, tests using other fluids were similarly performed under different temperature conditions, and similar results were obtained.

Test Example 3

In order to confirm the influence of the temperature of the packed tofu on the determination method and determination device according to the present invention, the following tests were performed.

1) Preparation of Samples

The packed tofu obtained in the Preparation Example 1 was used as a test sample. Moreover, two kinds of samples were used, one which was cooled in a cooling pool at 48° F. and another which was cooled in the cooling pool at 85° F., both after heat coagulation. Furthermore, the non-defective product which was sufficiently coagulated and the defective product which was not sufficiently coagulated were respectively prepared for the two kinds of samples.

2) Test Method

The immediate packed tofu after heat coagulation and cooling were continuously transported by the conveyor belt 10 and the surface temperatures at the measurement points C1 and C2 were measured, similarly to the Test Example 2. Moreover, the room temperature during measuring was set in a range from 60 to 68° F.

Then, the difference between the surface temperatures at the measurement points C1 and C2 of 245 packed tofu was examined.

3) Test Results

Figure 5:
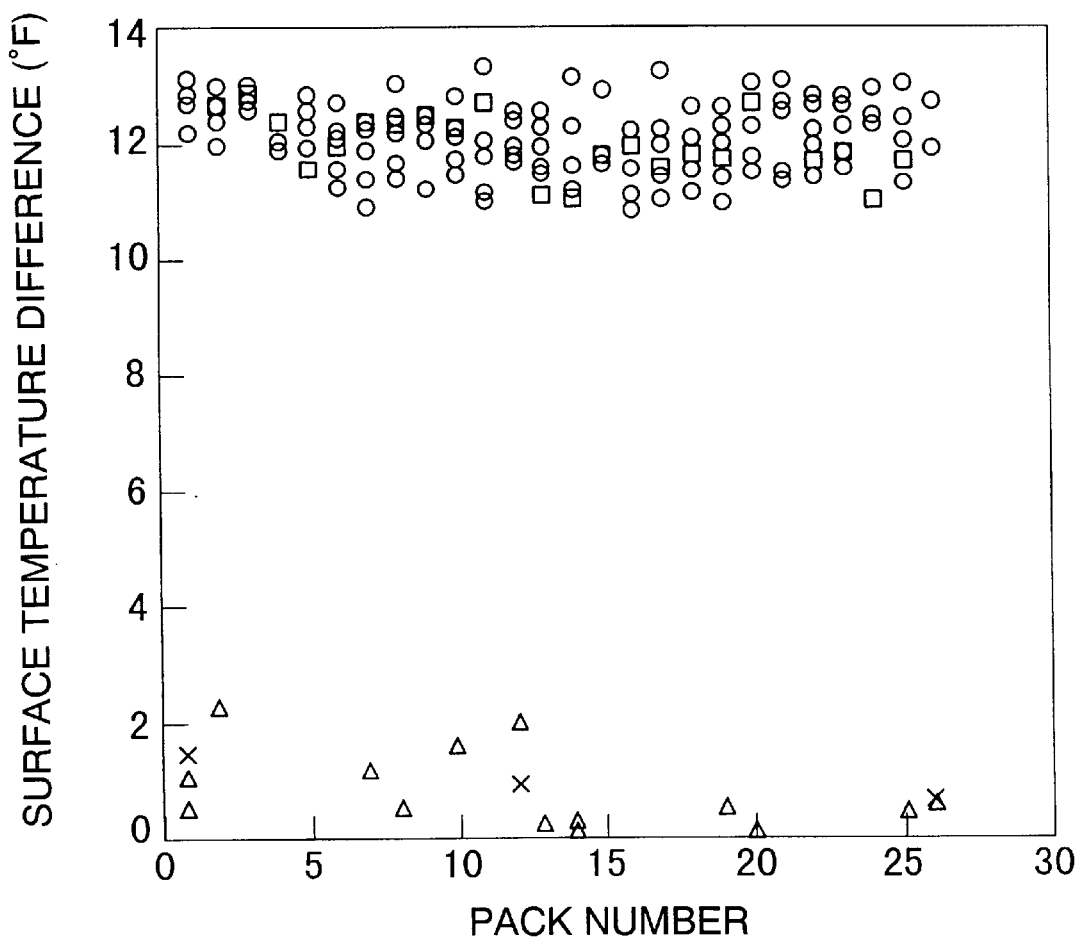
FIG. 5 is a graph showing the difference between the surface temperatures of the packed tofu when the temperature of the packed tofu is different.

The test results are shown in FIG. 5. In FIG. 5, the transverse axis indicates the pack number of the packed tofu (this number indicates the position of the packed tofu in the cooling pool), and the longitudinal axis indicates the difference between the surface temperatures at the measurement points C1 and C2.

In FIG. 5, the symbol "○" denotes the non-defective product obtained under conditions in which the cooling temperature is 48° F., the symbol "□" denotes the non-defective product obtained under conditions in which the cooling temperature is 85° F., the symbol "Δ" denotes the defective product obtained under conditions in which the cooling temperature is 48° F., and the symbol "X" denotes the defective product obtained under conditions in which the cooling temperature is 85° F.

It is clear from FIG. 5 that the non-defective products (○ and □) have a difference between the surface temperatures in a range of 12±2° F., and the defective products (Δ and X) have a difference between the surface temperatures in a range of 1±1° F., independent of the cooling conditions of the packed tofu, namely the temperature of the packed tofu. In other words, it is confirmed that the present invention can determine whether the products are non-defective, independent of the temperature of the packed tofu.

As this test result, it was confirmed that the determination method and the determination device of the present invention could always determine the fluidity of the fluid maintaining high accuracy, independent of the temperature of the fluid.

Moreover, tests using other fluids were similarly performed under different temperature conditions, and similar results were obtained.

Test Example 4

In order to examine the relationship between the environmental temperature of the packed fluid and the determination accuracy of the determination method and the determination device according to the present invention, the following tests were performed.

1) Preparation of Samples

The packed tofu obtained in the Preparation Example 1 was used as a test sample. Moreover, two kinds of samples comprising the non-defective product which was sufficiently coagulated tofu and the defective product which was not sufficiently coagulated tofu were prepared.

2) Test Method

The surface temperature of the packed tofu was measured using the determination device 1 of the Example 1. Moreover, when the conveyor belt 10 was stopped and the packed tofu was cooled at a room temperature (67.5° F.), the surface temperature of the pack was periodically measured. Furthermore, the determination of whether the packed tofu is non-defective or defective based on the measurement results was not performed. The difference between the surface temperatures calculated by the arithmetic means was output to the recorder, and recorded.

Such test was performed using the 3 non-defective products which were completely coagulated and the 3 defective products which were not completely coagulated.

3) Test Results

Figure 6:
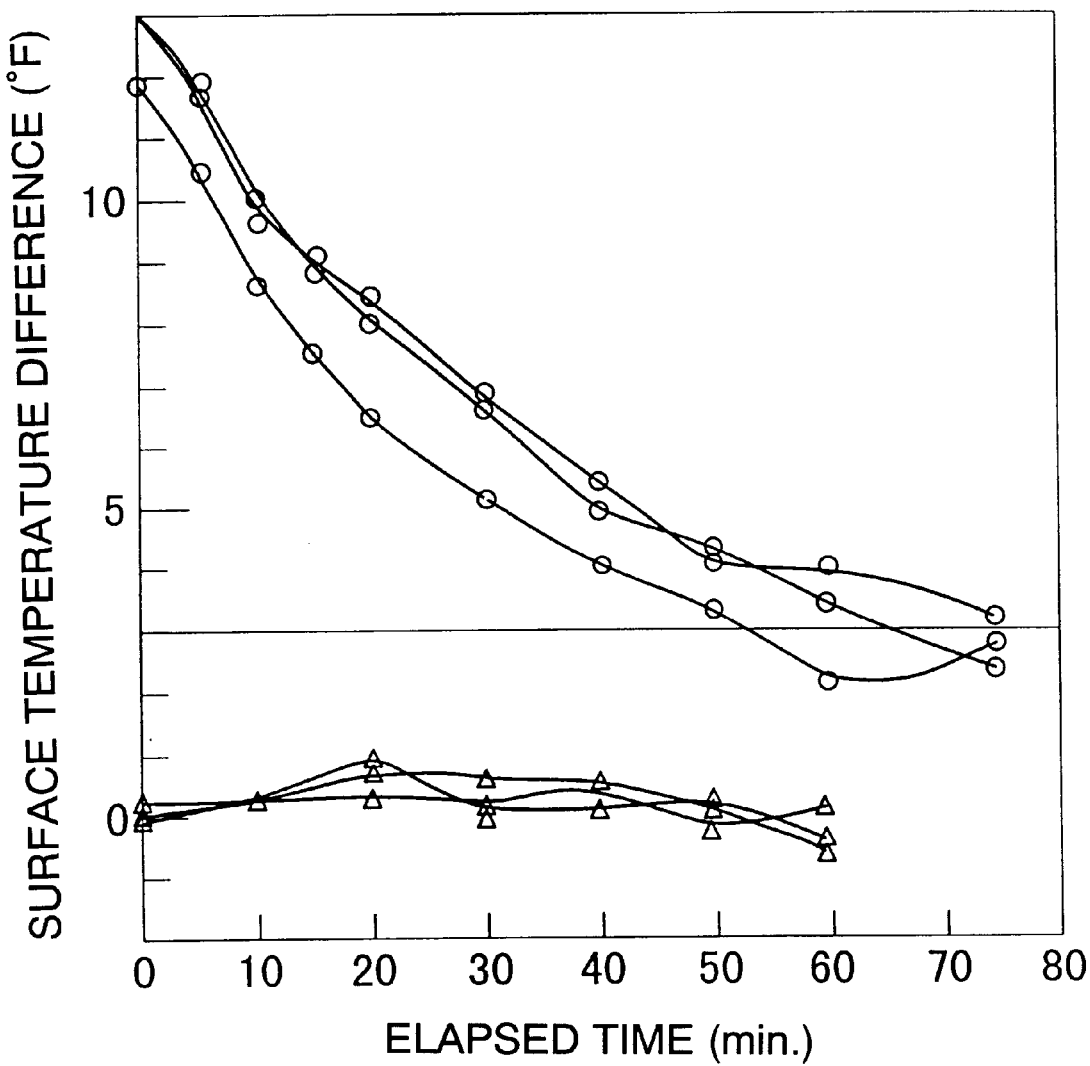
FIG. 6 is a graph showing the difference between surface temperatures of the packed tofu with respect to elapsed time.

The test results are shown in FIG. 6. In FIG. 6, the transverse axis indicates the elapsed time after the packed tofu was removed from the cooling pool, and the longitudinal axis indicates the difference between the temperatures (surface temperature difference) at the measurement points C1 and C2. In FIG. 6, the symbol "○" denotes the non-defective product which was completely coagulated, and the symbol "Δ" denotes the defective product which was not completely coagulated.

It is clear from FIG. 6 that after time has elapsed, the difference between the surface temperatures at C1 and C2 does not change in the defective packed tofu (Δ). In contrast, in the non-defective packed tofu (○), there is a tendency that the difference between the surface temperatures at C1 and C2 gradually decreases when the measurement begins.

After 60 minutes has passed since the measurement, the difference between the surface temperatures significantly decreases in the non-defective packed tofu (○); therefore, the determination of whether the product is defective (△) can be difficult.

It was confirmed from this test result that the measurement of the surface temperatures at two measurement points was preferably performed under conditions in which the difference between the temperature of the packed tofu and the environmental temperature is large. Moreover, when the packed fluid is non-defective, the temperature distribution does not dissipate in air after leaving for a long time, such as 60 minutes, after the surface temperature distribution is formed. Therefore, it was confirmed when the environmental temperature somewhat changed, as long as the temperature was early measured, the environmental temperature did not influence on determination accuracy in the determination method and the determination device according to the present invention. In other words, it was confirmed that according to the determination method and the determination device of the present invention, the fluidity of the fluid can be determined while maintaining excellent stability against the change of the environmental temperature.

Moreover, tests using other fluids were similarly performed under different temperature conditions, and similar results were obtained.

Example 2

The determination device 31 shown in FIG. 2 was prepared by providing the defective product discarding means 20, etc. with the determination device 1 prepared in the Example 1. The fluidity of the packed tofu prepared in the Preparation Example 1 was determined using the determination device 31.

(1) Measurement of the Surface Temperature

The immediate packed tofu after heat coagulation and cooling were continuously transported by the conveyor belt 10 and stored in a freezer at 41° F. However, the packed tofu was transported by placing on the conveyor belt 10 of the determination device 1 before storage in the freezer.

The transport speed of the conveyor belt 10 was set to 23 m/min. The signal processor 6 sampled the difference between the measurement values of the temperature sensors 2 and 3 at a frequency of 1 kHz. After the input of the trigger from the passing sensor 7, the signal processor 6 calculated the average of 8 times of samplings. The average of 8 times of samplings was set as a standard value. Moreover, the transport distance of the packed tofu for 8 times of samplings was 3 mm.

3) Determination of the Defective Products

The standard value of the signal processor 6 was set to 6° F., in advance. When the difference between the values measured by the temperature sensors 2 and 3 is larger than the standard value, 6° F., the signal processor 6 output the defective products discarding signal via the output line 6a, and the defective product was discarded by the defective product discarding means 20.

18,000 packed tofu were determined for 180 minutes, and 9 defective products were discarded.

Moreover, when all packed tofu were opened after the determination and the coagulation state of the tofu in the pack was examined, the packed tofu which were judged as defective products were mostly not coagulated. It was clear that these defective products could not be shipped. Moreover, all the packed tofu which were judged as non-defective products were completely coagulated. The defective product was not absolutely mixed with the non-defective products. It was confirmed from this Example that the determination method of the present invention has extremely high accuracy.

Industrial Applicability

According to the present invention, the fluidity of the fluid can be determined without breaking or opening the pack and without denaturing of the fluidity. In addition, the determination can be performed with high speed; therefore, the present invention can be used on a continuous type large scale manufacture line. Moreover, the present invention can determine all products. Furthermore, a structure of the use device is simple, and costs of investment and running for the device are reduced.

In particular, when the determination using the difference between the surface temperatures at the two measurement points of the pack, the fluidity can be determined maintaining stability and high accuracy, independent of the influences such as a change of the environmental temperature, a temperature of the fluid, etc.

What is claimed is:

1. A method for determining the fluidity of a fluid in a pack that is moving comprising the steps of:
   locating at least two measurement points on the surface of the pack,
   measuring the surface temperatures of the pack at the two located measurement points,
   determining a difference between the measured surface temperatures of the pack at the two measurement points,
   comparing the difference between the measured surface temperatures with a predetermined standard value between a surface temperature difference of the fluid in a solid state and a surface temperature difference of the fluid in a liquid state, and
   determining whether the fluid is in a solid or liquid state based on whether the difference between the surface temperature is larger than the standard value.

2. A method as claimed in claim 1, wherein the measurement points include a first measurement point located on the approximate center position of the side of the pack.

3. A method as claimed in claim 2, wherein the measurement points include a second measurement point located above the first measurement point.

4. A method as claimed in claim 1 wherein the measurement of the surface temperatures of the pack is performed under conditions in which there is a difference between the temperature of the packed fluid and an ambient temperature in a room in which the pack is located.

5. A method as claimed in claim 1 wherein the measurement of the surface temperatures of the pack is performed using a non-contact type temperature sensor.

6. A method as claimed in claim 2, wherein the measurement of the surface temperatures of the pack is performed under conditions in which there is a difference between the temperature of the packed fluid and an ambient temperature in a room in which the pack is located.

7. A method as claimed in claim 3, wherein the measurement of the surface temperatures of the pack is performed under conditions in which there is a difference between the temperature of the packed fluid and an ambient temperature in a room in which the pack is located.

8. A method as claimed in claim 2, wherein the measurement of the surface temperatures of the pack is performed using a non-contact type temperature sensor.

9. A method as claimed in claim 3, wherein the measurement of the surface temperatures of the pack is performed using a non-contact type temperature sensor.

10. A method as claimed in claim 4, wherein the measurement of the surface temperatures of the pack is performed using a non-contact type temperature sensor.

11. A method as claimed in claim 6, wherein the measurement of the surface temperatures of the pack is performed using a non-contact type temperature sensor.

12. A method as claimed in claim 7, wherein the measurement of the surface temperatures of the pack is performed using a non-contact type temperature sensor.

13. A device for determining the fluidity of a fluid in a moving pack comprising:

a non-contact type temperature sensor for measuring a surface temperature at each of at least two measurement points located at different positions on a surface of the moving pack; and an arithmetic means electrically connected with the non-contact type temperature sensor for calculating the difference in surface temperatures between the two measurement points, said arithmetic means having a stored predetermined standard value of the surface temperature difference between a fluid pack in a solid state and in a liquid state and means for comparing the calculated difference with said predetermined standard difference value, and determining whether the fluid is in a liquid or solid state based on whether said calculated difference between the surface temperatures is larger than the standard value.

14. A device as claimed in claim 13 further comprising:

a defective product determination signal output means which outputs the determined result of whether the fluid is in a liquid or solid state as a defective product determination signal.

15. A device as claimed in claim 14, further comprising:

a transport means for transporting the pack after the measurement of the surface temperature of the pack by the non-contact type temperature sensor; and a defective product discarding means for discarding a pack transported by the transporting means from a transporting line in response to the defective product determination signal outputs from the defective product determination signal output means.

* * * * *